United States Patent
Fibi

(10) Patent No.: US 8,632,505 B2
(45) Date of Patent: Jan. 21, 2014

(54) SYRINGE ACCESSORY DEVICE

(75) Inventor: Mathias Fibi, Marburg (DE)

(73) Assignee: Novartis Vaccines & Diagnostics, GmbH, Marburg (DE)

( * ) Notice: Subject to any disclaimer, the term of this patent is extended or adjusted under 35 U.S.C. 154(b) by 704 days.

(21) Appl. No.: 11/886,557

(22) PCT Filed: Mar. 15, 2006

(86) PCT No.: PCT/EP2006/060759
§ 371 (c)(1),
(2), (4) Date: Aug. 17, 2009

(87) PCT Pub. No.: WO2006/097492
PCT Pub. Date: Sep. 21, 2006

(65) Prior Publication Data
US 2009/0318879 A1    Dec. 24, 2009

(30) Foreign Application Priority Data
Mar. 16, 2005    (EP) ..................................... 05102085

(51) Int. Cl.
*A61M 5/00*    (2006.01)
(52) U.S. Cl.
USPC ......................................... 604/208
(58) Field of Classification Search
USPC ......................................... 604/208, 207, 235
See application file for complete search history.

(56) References Cited

U.S. PATENT DOCUMENTS

| | | | |
|---|---|---|---|
| 2,118,221 A | 5/1938 | Montuori | |
| 3,833,030 A | 9/1974 | Waldbauer, Jr. et al. | |
| 4,769,026 A * | 9/1988 | Strung | 604/415 |
| 5,487,738 A | 1/1996 | Sciulli et al. | |
| 5,951,526 A | 9/1999 | Korisch et al. | |
| 2004/0162528 A1 * | 8/2004 | Horvath et al. | 604/207 |

FOREIGN PATENT DOCUMENTS

| LU | 85983 A1 | 2/1987 |
|---|---|---|
| LU | 85983 A1 * | 2/1987 |

OTHER PUBLICATIONS

International Search Report mailed Jul. 4, 2006, for PCT/EP06/60759 filed Mar. 15, 2006, 5 pages.

* cited by examiner

*Primary Examiner* — Nicholas Lucchesi
*Assistant Examiner* — Jenna Zhang
(74) *Attorney, Agent, or Firm* — Regina Bautista

(57) ABSTRACT

The invention provides a syringe accessory device for adjustment of a predefined partial syringe dosage comprises a recess (10) for receiving a syringe body (14). Additionally, within a single portion (12) a slot (16) is located. Within the slot (16) a syringe flange (18) or finger grip can be held. To obtain a predefined dosage of liquid within the chamber of the syringe body (14), a plunger (26) is pressed in the chamber (14) in the direction of the arrow (38) until the plunger head (44) contacts a stopping means (24) whereby the stopping means is performed by a stopping surface (24) of the single portion (12). The invention further provides a kit comprising said syringe accessory device and its use for adjusting defined liquid dosages in syringes.

17 Claims, 2 Drawing Sheets

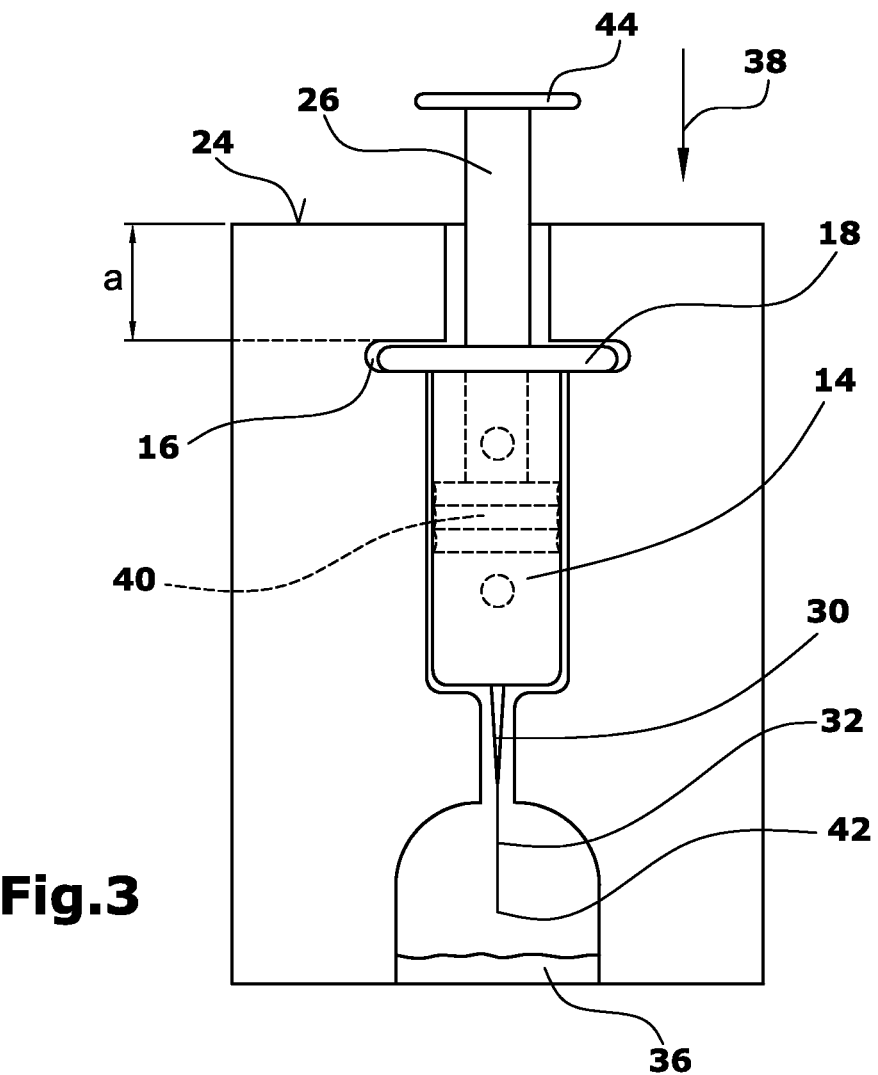

SYRINGE ACCESSORY DEVICE

The invention relates to a syringe accessory device for adjustment of a predefined partial syringe dosage, a kit comprising said syringe accessory device and its use for adjusting defined liquid dosages in syringes.

To fill a syringe body of a syringe with a predefined amount of liquid, in a first step a larger amount of liquid than the necessary dosage is taken up or sucked into the syringe body. Thereafter, liquid is emitted from the syringe body till the desired dosage is within the syringe body. Therefore, the syringe body is marked with lines defining a specific dosage. This way of filling a syringe body with a desired dosage is very complicated and time-consuming. Additionally, it is not guaranteed that the exact desired amount of liquid is within the syringe body. This kind of dosing is always inexact and particular vulnerable to user error.

A similar problem arises if a pre-filled syringe has to be partially emptied to adapt the dosage to a specific need, e.g. syringes for vaccination where "half-doses" for children have to be provided.

A syringe accessory device is described in U.S. Pat. No. 4,357,971. This device has a recess for a syringe body and a slot for holding a syringe flange. Additionally, a stopping member used to define a distance between the slot and the syringe flange or finger grip is adjustably connected to the device with a threaded shank. For moving the stop member, the threaded shank is connected with a wheel threaded on the shank. This device is made for private use, particularly for elderly people having problems to fill in the correct dosage in the above described way. The syringe accessory device as described in U.S. Pat. No. 4,357,971 is, for example, used to inject insulin or the like. To do so, the syringe body is filled with the liquid by sucking the liquid through the needle. Additionally, the syringe is located within the syringe accessory device whereby the syringe body located in the recess and the syringe flange or finger grip is located in the slot. Thereafter, the stop member is adjusted to the desired dosage by moving the stop member. Then, the stop member is pivoted so that it is located above the syringe flange. Thereafter, the plunger of the syringe is moved farther into the syringe body until the plunger head is stopped by the stop member. Thereby liquid is emitted from the needle into the surrounding air. The needle extends from the syringe accessory device so that the needle can be inserted in the human body, e.g. into a vein. Thereafter, the stop member is pivoted so that the plunger head is released and the plunger can be pressed in the syringe body to emit the liquid into the vein.

The syringe accessory device as described in U.S. Pat. No. 4,357,971 is relatively complicated. It is particularly necessary to adjust the stop member to the exact desired dosage. This may lead to the same mis-dosing as just looking on marks on the syringe body.

It is an object of the invention to provide a syringe accessory device for adjustment of a predetermined partial syringe dosage making the handling of the syringe and the adjustment of the dosage easier. This and other objects are achieved by a syringe accessory device of the invention. The invention thus provides (1) a syringe accessory device for adjustment of a predefined partial syringe dosage, comprising:
   a recess (10) for a syringe body (14),
   a slot (16) for holding a syringe flange (18) and
   a stopping means (24) for stopping a movement of a syringe plunger (26),
   the stopping means being located at a distance to the slot (60) so that the predefined dosage remains within the syringe body (14),
characterized in that said slot (16) and said stopping means (24) have a fixed distance (a) and are provided in one single portion (12).

The syringe accessory device may be used for any fixed does application and is particularly useful for preparing "half-dose" vaccines for children.

The invention further provides
(2) a kit comprising at least one syringe accessory device as defined in (1) above and syringes adapted for said at least syringe accessory device;
(3) a method for adjusting the liquid dosage in syringes utilizing the accessory device as defined in (1) above;
(4) the use of a syringe accessory device as defined in (1) above for preparing a defined liquid dosage of a medicament; and
(5) a method for administering a defined liquid dosage to a patient by means of a syringe, said method comprising adjusting the content of the syringe by utilizing a syringe accessory device.

The syringe accessory device has a recess for a syringe body and a slot for holding a syringe flange or finger grip. Additionally, the syringe accessory device comprises a stopping means for stopping a movement of a syringe plunger within the syringe body. To stop the movement of the syringe plunger, a plunger head or the like may touch the stopping means. This stopping means is located in a distance to the slot, so that the position and the movement of the syringe plunger is stopped, and the plunger foot, i.e. the end portion of the plunger being located within the syringe body, is located in a distance to the bottom of the syringe body or chamber, so that within this part of the chamber the predefined dosage of the liquid is stored. Thereby the distance of the plunger foot to the bottom of the syringe chamber relates to the distance between the slot and the stopping means. According to the invention, the slot and the stopping means having a fixed distance. This is particularly realized by providing the slot and the stopping means in one single portion, i.e. as a one-pieced unit. A fixed distance between the slot and the stopping means has the advantage that a disadjustment cannot occur. The reason for such a disadjustment could be that the accessory device is used for different dosages. This is not possible with the device according to the invention. Additionally, the handling of the accessory device according to the invention is much easier. Moreover, the accessory device of the present invention guarantees a consistent standard does, even if multiple users. It may be used, for example, in a clinical trial setting Preferably, an outer surface of the single portion of the accessory device is used as a stopping surface so that this surface forms the stopping means. Thus, the function of the device can be clearly seen by a user and the device is easy to handle. Thus, the danger to inject a wrong amount of liquid due to misalignment or misjudgment is minimized.

According to a preferred embodiment of the invention, the accessory device and particularly the single portion has a needle recess. Within the needle recess, the needle of the syringe is received during dosing. Thus, the needle is protected by the recess surrounding the needle at least partly. Particularly, the tip of the needle is located within the needle recess so that it is protected from a push or the like.

Additionally, in a preferred embodiment, the syringe accessory device according to the invention comprises a liquid receiving means. This liquid receiving means which can comprise a liquid-absorbing means, like a cushion or the like, is used for receiving the liquid emitted from the syringe during dosing. Thus, the liquid is not emitted into the air so that it cannot cause any health problems or the like.

Additionally, the syringe accessory device according to the invention may comprise a standing portion so that the syringe accessory device can be located in an upright position. In this position, it is easy to store the device and to dose the liquid. The standing portion is preferably a part of said single portion so that in a preferred embodiment the whole syringe accessory device forms one piece.

A preferred embodiment of the syringe accessory device according to the invention comprises a removing means. This removing means is used to remove the syringe located within the recess of the single portion after the dosing has been performed. Preferably, the removing means comprises an injector means which is preferably movably held in the single portion. Particularly, the injector means comprises a movable, particularly slidably held plunger or the like being located within the single portion, whereby the injector means contacts the syringe preferably at the syringe body. With the removing means it is much easier to remove the syringe from the accessory device, particularly out of the body recess formed within the single portion.

In a further preferred embodiment the syringe accessory device is suitable to be used to prepare a pediatric vaccine (such as a flu vaccine) which requires a lower dose than a vaccine for an adult. In case of flu recommended for inactivated influenza vaccines are 15 µg of each HA component per vaccine dose for persons 3 years of age and over and 7.5 µg of each HA per vaccine dose for children under 3 years of age.

The syringe accessory device according to the invention will be described in more detail with reference to the drawings, which are however not to be construed so as to limit the invention.

FIG. 3 shows a front view of the syringe accessory device together with a syringe being located in the device.

Figure 1:
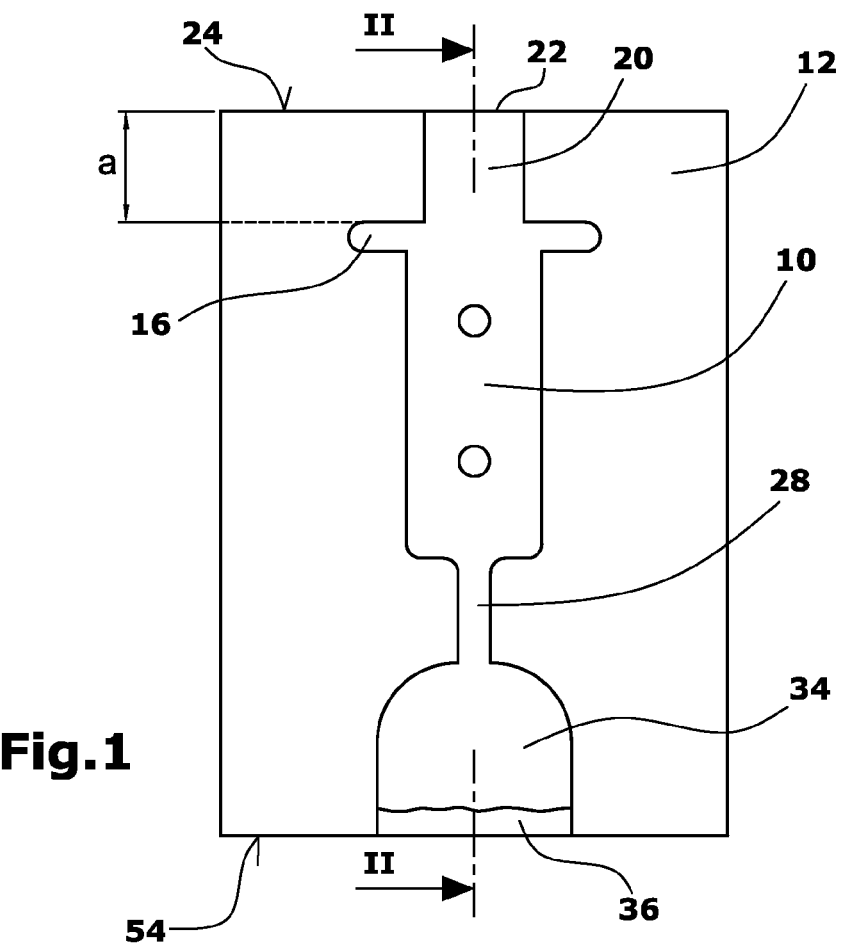
FIG. 1 shows a front view of the syringe accessory device without syringe.

The syringe accessory device for adjustment of a predefined partial syringe dosage comprises a recess 10 within a single portion 12 wherein in the shown embodiment the whole syringe accessory device is one-pieced. Within the recess 10, a syringe body 14 (FIG. 3) will be located. Adjacent to the recess 10, a slot 16 is located within this one-pieced device. The slot 16 is used to hold a syringe flange 18 or finger grip of the syringe.

In line with the recess 10 a recess 20 is located within the body having an opening 22 being located in an surface 24. Within the recess 20, a plunger 26 (FIG. 3) of the syringe is located.

Another recess 28 is also located in line with the body recess 10 on the opposite side of the plunger recess 20. Within the recess 28, a projection 30 holding the needle 32 is located.

The needle 32 extends in a needle recess 34. At the bottom of the needle recess 34, a liquid receiving means 36 being a cushion or the like is located whereby the liquid receiving means 36 comprises or is made from a liquid absorbing material.

According to the invention, the stopping means is built by the outer stopping surface 24. The surface 24 is flat and parallel to the slot 16. For the dosing of the liquid contained within the chamber of the syringe body 14, the distance 'a' between the slot 16 and the stopping surface 24 is fixed. Thus, by pressing the plunger 26 in the direction of the arrow 38 (FIG. 3), a plunger foot 40 is moved downward within the chamber of the syringe body 14 so that liquid is ejected from a needle tip 42. The ejected liquid will be received by the liquid receiving means 36.

The movement of the plunger 26 is stopped when a plunger head 44 of the plunger 26 contacts the stopping surface 24. In this state, the amount of liquid within the chamber of the syringe body 14 is the predefined dosage.

Figure 2:
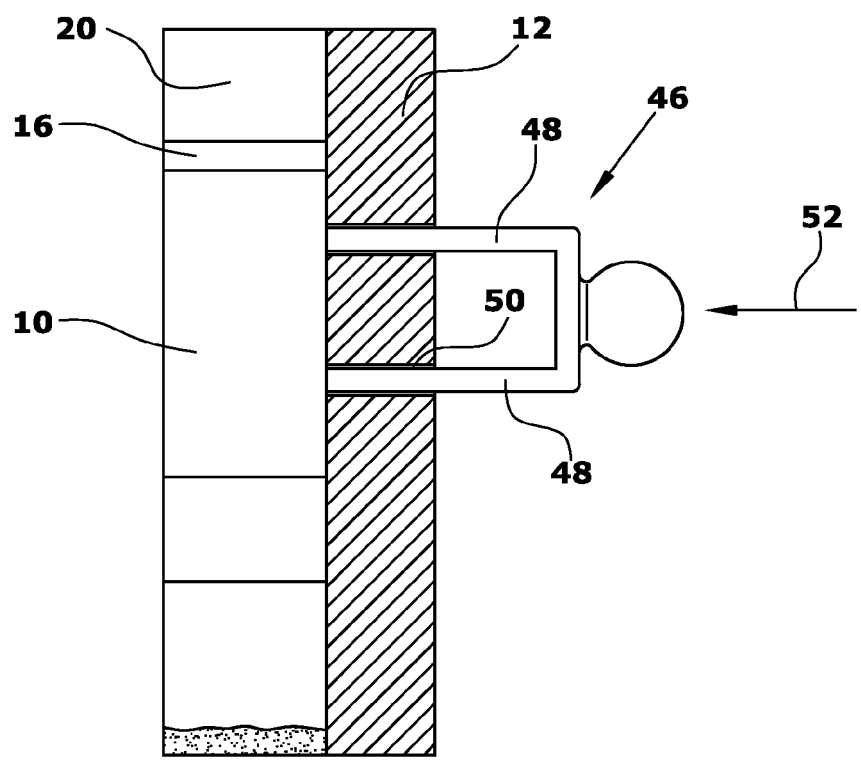
FIG. 2 shows a sectional view along the line II-II in FIG. 1.

To remove the syringe out of the single portion 12, a removing means 46 (FIG. 2) is located in the single portion 12. As shown in this embodiment, the removing means has two ejector means 48 being connected to each other. The ejector means 48 are slidably held within openings 50 in the single portion 12. The openings 50 are located at the height of the body recess 10 so that the ejector means or plungers 48 are pushed against the syringe body 14 in the direction of the arrow 52. Thus, it is easy to remove the syringe from the syringe accessory device.

Additionally, the syringe accessory device has a standing portion 54 whereby the standing portion 54 is flat and parallel to the stopping surface 24. The standing portion 54 is located on the opposite side of the stopping surface 24.

The syringe accessory device may have a means for filling the syringes such as means for taking up the liquid from a container.

The kit of embodiment (2) of the invention comprises at least a syringe accessory device as defined hereinbefore and syringes adapted for said device. In a preferred embodiment where different dosages are contemplated (e.g. adult and pediatric) the kit contains two or more syringe accessory devices adapted for said different dosages.

The syringes of the kit may be filled or empty. In the latter case, the kit may further contain a container with liquid medicament for filling the syringes.

The invention claimed is:

1. A syringe accessory device for adjustment of a predefined partial syringe dosage, comprising: a recess (10) for a syringe body (14), a single slot (16) for holding a syringe flange (18) and an outer stopping surface (24) that stops a movement of a syringe plunger (26), the outer stopping surface being located at a distance to the slot (60) so that the predefined dosage remains within the syringe body (14), characterized in that said single slot (16) and said outer stopping surface (24) have only a single fixed distance (a) and are provided in a one-piece unit (12).

2. The syringe accessory device of claim 1, characterized in that said outer stopping surface (24) is parallel to said single slot (16).

3. The syringe accessory device according to claim 1 or claim 2, characterized by a needle recess (34) for receiving a needle (32) of the syringe during dosing.

4. The syringe accessory device of claim 3, characterized in that a tip (42) of said needle (32) is located within said needle recess (34).

5. The syringe accessory device of claim 3, characterized by a liquid receptacle (36) configured to receive liquid emitted from said syringe body (14) during dosing.

6. The syringe accessory device of claim 5, characterized in that said liquid receptacle comprises a liquid absorbing material (36).

7. The syringe accessory device of claim 5, characterized in that said liquid receptacle (36) is located opposite said needle tip (42).

8. The syringe accessory device according to claim 1 or claim 2, characterized by a standing portion (54) for locating the syringe accessory device in an upright position.

9. The syringe accessory device of claim 8, characterized in that said standing portion (54) is a part of said one-piece unit (12).

10. The syringe accessory device of claim 8, characterized in that said standing portion has a standing surface (54) opposite said outer stopping surface (24).

11. The syringe accessory device according to claim 2, characterized by a syringe ejector (46) configured to eject the syringe out of the syringe accessory device.

12. The syringe accessory device of claim 11, characterized in that said syringe ejector (48) is movably held in an opening (50) of said one-piece unit (12).

13. The syringe accessory device according to claim 1 or claim 2 which is suitable to prepare a pediatric vaccine which requires a lower dose than an adult vaccine.

14. A kit comprising at least one syringe accessory device according to claim 1 or claim 2 and syringes adapted for said at least syringe accessory device.

15. A method for adjusting the liquid dosage in syringes which comprise reducing the content of the syringes by applying said syringes to an syringe accessory device according to claim 1 or claim 2.

16. A method for preparing a defined liquid dosage of a medicament contained within a syringe comprising placing the syringe in the recess (10) of the syringe accessory device of claim 1 or claim 2 such that a flange of the syringe is located in the single slot (16) and depressing a plunger of the syringe to eject liquid from the syringe until a plunger head of the syringe contacts the stopping surface (24) of the syringe accessory device.

17. A method for administering a defined liquid dosage to a patient by means of a syringe, said method comprising adjusting the content of the syringe by utilizing a syringe accessory device according to claim 1 or claim 2.

\* \* \* \* \*